United States Patent [19]
Weindel

[11] Patent Number: 5,830,762
[45] Date of Patent: Nov. 3, 1998

[54] MATERIALS AND METHODS RELATING TO BINDING ASSAYS

[75] Inventor: Kurt Weindel, Wieoenbach, Germany

[73] Assignee: Boehringer Mannheim GmbH, Mannheim, Germany

[21] Appl. No.: 796,806

[22] Filed: Feb. 6, 1997

[30] Foreign Application Priority Data

Feb. 6, 1996 [GB] United Kingdom .................. 9602323

[51] Int. Cl.$^6$ .......................... G01N 33/50; G01N 33/53
[52] U.S. Cl. .................................. 436/8; 435/4; 435/7.1; 435/7.92; 436/501; 436/518
[58] Field of Search ................................. 435/4, 7.1, 7.5, 435/7.92, 7.93, 7.94, 7.95; 436/501, 518, 543, 544, 547, 548, 8

[56] References Cited

U.S. PATENT DOCUMENTS 5,424,220  6/1995  Goerlach-Graw et al. ............. 436/568

FOREIGN PATENT DOCUMENTS 0304202  2/1989  European Pat. Off. .
WO93/08472  4/1993  WIPO .

OTHER PUBLICATIONS

Noe et al., *Brit J. Haematology* 80:285–292, 1992.
Lindsay et al., *Clin. Biochem* 28(4):395–400, 1995.
Franek et al., *J. Agric. Food Chem.* 42:1369–1374, 1994.
Keilacker et al., *Eur. J. Clin. Chem. Clin. Biochem* 29:555–563, 1991.

*Primary Examiner*—Robert D. Budens
*Attorney, Agent, or Firm*—Dann, Dorfman, Herrell and Skillman

[57] ABSTRACT

Methods of optimising binding assays are disclosed using binding agents having binding sites specific for an analyte by varying the density of binding sites on a solid phase, advantageously extending the working range of the assay and/or improving the precision of the assay within a given range. Processes for manufacturing an assay kit following the optimisation method and to methods of carrying out assays for analytes using these assay kits are also provided.

16 Claims, 8 Drawing Sheets

MATERIALS AND METHODS RELATING TO BINDING ASSAYS

FIELD OF THE INVENTION

The present invention concerns materials and methods relating to binding assays, and in particular to methods for optimising binding assays using binding agents having binding sites specific for an analyte by varying the density of binding sites on a solid phase, to processes for manufacturing an assay kit following the optimisation method and to methods of carrying out assays for analytes using these assay kits.

BACKGROUND OF THE INVENTION

It is known to measure the concentration of an analyte, such as a drug or hormone, in a liquid sample by contacting the liquid with a binding agent having binding sites specific for the analyte, separating the binding agent and measuring a value representative of the proportion of the binding sites on the binding agent that are occupied by analyte (referred to as the fractional occupancy). Typically, the concentration of the analyte in the liquid sample can then be determined by comparing the fractional occupancy against values obtained from a series of standard solutions containing known concentrations of analyte. Often these values are represented graphically as a dose response curve, which plots the assay response (e.g. the signal from a labelled developing reagent) against changes in analyte concentrations.

When assays are developed, it is conventional to optimise them, that is to say, to choose the physicochemical properties and concentrations of the assay reagents that yield maximum precision of measurement of analyte concentration in a useful working range, e.g. the clinical range of concentrations of a hormone. In the past, assay optimisation has been carried out by varying parameters such as the amount of binding agent or labelled developing agent used in the assay, or the affinity of the binding agent for the analyte.

In the field of immunoassay, competitive immunoassays have in general been carried out in accordance with design principles enunciated by Berson and Yalow, for instance in "Methods in Investigative and Diagnostic Endocrinology" (1973), pages 111 to 116. Berson and Yalow proposed that in the performance of competitive immunoassays, maximum sensitivity is achieved if an amount of binding agent is used to bind approximately 30 to 50% of a low concentration of the analyte to be detected. In non-competitive immunoassays, maximum sensitivity is generally thought to be achieved by using sufficient binding agent to bind close to 100% of the analyte in the liquid sample. However, in both cases immunoassays designed in accordance with these widely accepted precepts require the volume of the sample to be known and the amount of binding agent used to be accurately known or known to be constant.

More recently, this trend has changed and assays have been developed that measure the concentration of an analyte in a liquid sample using very small amounts of binding agent that bind only a small proportion of the analyte in the sample. In some cases, the binding agent is immobilised in the form of one or more small areas or "microspots", allowing the determination of one or more analytes in a sample to be carried out simultaneously. An example of this is EP-A-0304202 which discloses that assays which are independent of the volume of the sample and the amount of binding agent used can be obtained using an amount of binding agent less than 0.1 V/K moles located on a small area on a solid support, where V is the volume of the sample and K is the equilibrium constant of the binding agent for the analyte.

WO93/08472 discloses a method of further improving the sensitivity of binding assays by immobilising small amounts of binding agent at high density on a support in the form of a microspot. In this assay, a developing agent comprising a microsphere containing a marker, e.g. a fluorescent dye, is used to back-titrate the binding agent after it has been contacted with the liquid sample containing the analyte.

SUMMARY OF THE INVENTION

Broadly, the present invention relates to methods for fine-tuning binding assays so as to meet pre-selected design goals, such as broad dynamic or even linear ranges of measurement, or high analytical sensitivity, or preferably both of these. This is based on the finding that, in an assay for an analyte using a binding agent having binding sites specific for the analyte, it is possible to modulate dose response curve profiles, and corresponding features of the assay, by adjusting the binding site density on a solid phase of a test carrier.

Accordingly, in one aspect the present invention provides a method for optimising a binding assay using a binding agent having binding sites specific for an analyte, the binding agent being immobilised on a solid phase or becoming immobilised during the course of the assay, wherein the method comprises adjusting the density of the binding sites on the solid phase. It is then possible to examine the dose response curves obtained at different densities of binding sites, selecting the density at which a feature or property of the assay is optimised.

Thus, the present invention provides a method for optimising a binding assay using a binding agent having binding sites specific for an analyte, the binding agent being immobilised on a solid phase or becoming immobilised during the course of the assay, the method comprising:

(a) determining a dose response curve for a given density of binding agent on the solid support;

(b) adjusting the density of the binding agent on the solid support to modulate the dose response curve;

(c) optionally repeating steps (a) and (b); and, (d) selecting the density of binding agent providing the dose response curve having a desired profile.

In the above method, the steps (a) and (b) can be repeated until a suitable binding site density is found, i.e. one that has a desired set of performance characteristics.

In this application, "optimisation" refers to the process of designing or developing an assay system so as to improve one or more performance characteristics of the assay, such as improving its working range and/or improving its precision within a particular working range of analyte concentrations, ie minimising the random error incurred in the measurement of analyte concentration. This process may involve improving the sensitivity of the assay, that is the ability of the assay system to determine low concentrations of analytes, represented numerically by the lowest analyte concentration distinguishable from zero (the "detection limit"). As mentioned above, in the prior art, assay optimisation relied on varying parameters such as the amount of binding agent or labelled developing agent used in the assay, or the affinity of the binding agent for the analyte. In contrast, the present invention varies the density of binding sites on the solid phase to optimise an assay system, either alone or in combination with known optimisation techniques.

In a further aspect, the present invention provides a process for manufacturing an assay kit following the above optimisation method, the process comprising immobilising binding agent having binding sites specific for an analyte on a solid phase, wherein the binding agent is immobilised on the solid phase to provide a density of binding sites determined using said optimisation method.

In a further aspect, the present invention provides a process for manufacturing an assay kit following the above optimisation method, the process comprising manufacturing a functionalised solid phase capable of binding to derivatised binding agent having binding sites specific for an analyte, wherein the binding agent is immobilised on the solid phase prior to or during the course of the assay to provide a density of binding sites determined using said optimisation method.

In a further aspect, the present invention provides a process following the manufacture of an assay kit, the process comprising the steps of:

(a) contacting the solid phase with a liquid sample so that a fraction of the binding sites are occupied by analyte in the sample;

(b) measuring a value of a signal representative of the fraction of the binding sites occupied by the analyte; and, (c) comparing the value to the dose response curve to determine the concentration of the analyte in the liquid sample.

Thus, we have found that adjusting the density of the binding sites on the solid phase has an effect on the ligand-receptor interaction between an active solid phase component, and a corresponding, initially soluble, binding partner. In this connection, the solid phase component may be a binding agent that is immobilised on a solid phase carrier prior to carrying out the assay or a capture agent that can bind to soluble binding agent.

The density of binding sites can be adjusted in a number of different ways, depending on whether the binding agent is immobilised on the solid phase prior to carrying out the assay or becomes immobilised on the solid phase during the course of the assay, e.g. by using an activated solid phase capable of capturing soluble binding agent. An example of this latter approach is to activate a solid phase by coating it with avidin, and using soluble biotinylated binding agent, which has binding sites for the analyte, the binding agent being captured by the solid phase by the biotin-avidin interaction. Alternatively, the binding agent may be provided with an oligonucleotide tail which can be captured by complementary oligonucleotide sequence immobilised on a support, see WO 95/24649.

In the present invention, "adjustment of binding site density" on the solid phase refers to one or more of:

(a) adjusting the immobilised binding sites directly by changing the density of binding agent or capture agent immobilised on the solid phase; and/or, (b) adjusting the concentration of a soluble binding agent or capture agent exposed to the solid phase, thereby determining the amount of the agent that will be immobilised during a given period of time; and/or, (c) adjusting the incubation time allotted to immobilise the capture agent or the binding agent, thereby determining the portion of the agent that will be immobilised when a given fixed mass per volume of the agent is used; and/or, (d) adjusting the valency of the agent, e.g. whole agent, functional fragments thereof, or polymerized aggregates of either the intact molecule or a fragment thereof, thereby to change the number of binding sites.

Preferably, the effect of adjusting the binding site density is to change the dynamic or linear range of measurement of the assay and/or to improve sensitivity within a given range.

In one preferred method, the binding site density is adjusted at the time the binding agent or capture agent is immobilised on the support. Conveniently, this can be done by spraying droplets, e.g. using a modified ink-jet printing head, containing the binding agent or the capture agent onto the solid phase, and allowing the droplets to dry so that the agent becomes adsorbed onto the surface of the solid phase. The density of the binding agent or the capture agent can be controlled by varying the concentration of the agents in the droplets. Advantageously, when the concentration of the agent in the droplets is reduced, a filler substance such as a non-reactive protein is added to the solution to control adsorption onto the solid phase and/or to help to stabilise the agent in solution and/or to ensure saturation of the reaction site area, thereby helping to reduce non-specific binding to the solid phase.

Optionally, the density of binding agent or capture agent on the solid phase is selected so that it is different at different locations on the solid phase, e.g. by contacting the solid phase with varying concentrations of binding or capture agent so as to generate a plurality of reaction sites with different assay characteristics. This may extend the working range that can be determined for a given analyte using a test carrier comprising the solid phase. Additionally or alternatively, the methods described above can be used to construct solid phases in which binding agents having binding sites which are specific for different analytes are immobilised at discrete locations on the solid phase.

The present invention is particularly applicable to assays in which small amounts of binding are used, e.g. immobilised on a solid phase in the form of one or more individual reaction sites, e.g. as microspots. This format of assay is useful as it can be used to measure the concentration of many analytes simultaneously and is susceptible to miniaturisation.

In a further aspect, the present invention provides a solid support as obtainable by any one of the above methods.

In the present invention, the binding agent and analyte or the capture agent and the binding agent can be any molecular entities capable of binding one another in a specific manner, ie any species capable of acting as a ligand and a receptor.

Typically, one component of such a ligand-receptor system is macromolecular (e.g. the receptor), and the other component is a low molecular weight compound, e.g. a peptide, or even a small organic compound, e.g. with a molecular weight of less than 2000 dalton, ie a hapten. Examples of this sort of ligand-receptor binding pair are antigens and antibodies, hormones and hormone receptors, and biotin and (strept) avidin.

Alternatively, both components of the ligand-receptor system may be macromolecular. Examples of this sort of ligand-receptor interaction are hybridization reactions between DNA and DNA, DNA and RNA, or DNA and synthetic substances like PNA. Sugar and lectin interactions may span the range from low molecular weight compound (e.g. oligosaccharides): macromolecular compound interactions to interactions between two macromolecular components (e.g. lectins, or agglutinins, binding to glycosylated outer surface proteins of living cells).

Alternatively, ligand-receptor systems may also be composed of the interaction of two low molecular weight substances, e.g. the specific reaction of phenylboronic acids with salicylhydroxamic acids.

A number of interactions can occur in a binding assay between the binding agent (receptor) and the analyte (ligand) in the course of performing a given assay. These may include interactions between:

(a) the capture agent on the solid phase and a binding agent;
(b) the binding agent and analyte molecule(s);
(c) analyte molecule(s) and an indicator reagent; and,
(d) an indicator reagent and a secondary signalling reagent.

In some embodiments of the invention, a specific binding agent may be directly fixed on the solid phase of the test carrier, i.e. on the plastic or glass surface by physical adsorption. In other embodiments, the surface of the test carrier may be coated with a capture reagent that is able to specifically interact with and bind the binding agent, allowing it to be introduced into the reaction mixture in soluble form, and subsequently immobilised on the solid phase as part of the assay procedure.

DETAILED DESCRIPTION

Experimental

An immunoassay for total hIgE was chosen to demonstrate experimentally, the benefits of methods set out above.

The assay exemplified below used a miniaturised limited reagent solid phase having one or several spots, that is small, spatially isolated reaction sites. Monoclonal antibodies were used for both the binding agent, and the indicator reagent, with fluorescent microspheres (latex fluorobeads) used as labels. The labels were either directly attached to the indicator antibody, or the indicator antibody was digoxigenylated and the labels were conjugated to an affinity pure polyclonal anti-digoxigenin IgG. For detection, a laser scanning device employing confocal microscopy and PMT technology was used. Miniaturised black dyed polystyrene disposables with 2 reaction wells served as test carriers.

Two different kinds of microspots were investigated. Firstly, 5×5 spot arrays were produced by means of direct adsorption of jetted underivatised antibody onto the plastic wall of the test carriers, thus providing the basis for a typical sandwich type assay. In this case, adjustment of the binding site density was carried out by varying the concentration of the particular antibody in the jetting solution, with or without additional filler substance (i.e. dummy protein). The dummy protein helped to prevent adsorption of the agent on the walls of the jet device, or in order to stabilise the reagent of interest in solution.

Secondly, 5×5 spot arrays were produced by means of jetting conjugates of thermally treated BSA and streptavidin, which subsequently served as reaction sites for the immobilisation of biotinylated antibody during the assay. In this case, formation of reaction complexes and immobilisation the complexes occurred simultaneously. Assays of this format may be termed simultaneously delayed solid phase type assay. In this case, adjustment was carried out by varying the concentration of antibody in the first incubation step, or by varying the incubation time for the first step. Again, manipulations like these may be performed with or without additional filler (dummy) protein.

Application of antibodies or antibody fragments with different valency is applicable to both of the above cases, and was exemplified in the course of these studies for the second approach.

Glossary of terms used:
n.d.=not determined.
BSA=bovine serum albumin.
Mab=monoclonal antibody.
Pab=polyclonal antibody.
Fab=antigen binding fragment of an antibody.
hIgE=human immunoglobulin E.
<hIgE>=antibody specifically directed against hIgE.
DIG=digoxigenin.
<DIG>=antibody specifically directed against DIG.
AVG=mean value of replicate measurements.
SD=standard deviation of the mean value of replicate measurements.
LDD=least detectable dose, ie analytical sensitivity.
RT=room temperature.
Y/G=yellow-green dye (proprietary dye of Molecular Probes).
$\lambda_{ex}$=peak wavelength for excitation of a fluorescent dye.
$\lambda_{em}$=peak wavelength of emission from a fluorescent dye.

RESULTS

Directly Adsorbed Antibody

Test format:
5×5 spots of directly adsorbed Mab<hIgE>M.323+ myeloma IgE standards in horse serum, 1:2 diluted in phosphate buffer, 50 µl.
=>20 min incubation at RT with orbital shaking.
=>wash (=b/f-separation).
+conjugate Mab<hIgE>M.7H8-COOH-latex (Y/G), 0.025% solids, 50 µl.
=>20 min incubation at RT with orbital shaking.
=>wash (=b/f-separation).
=>measurement ($\lambda_{ex}$, 485 nm; $\lambda_{em}$ 530 nm).

With different concentrations of Mab<hIgE>M.323 in the jetting solution, the following dose responses expressed as arbitrary fluorescence units (AU) were obtained:

TABLE 1

| | | ← Mab<hIgE>M.323, [mg/ml] → | | | |
|---|---|---|---|---|---|
| | [U/ml] | 1 | 0.1 | 0.01[a] | 0.01[b] |
| Standard A | 0 | 212 | 331 | background | background |
| Standard B | 18.6 | 16627 | 14765 | 628 | 352 |
| Standard C | 72.4 | 29528 | 28774 | 1861 | 1059 |
| Standard D | 145 | 33042 | 30929 | 3692 | 1926 |
| Standard E | 291 | 35086 | 34405 | 7208 | 3871 |
| Standard F | 446 | 37148 | 34426 | 9407 | 4845 |

[a] = without dummy protein
[b] = with 1 mg/ml Mab<CK-MM>M.33(IgG) as dummy protein As can be seen from this data, with 1 mg/ml Mab<hIgE>M.323 a very sensitive (i.e. steep) dose response curve was obtained at the lower range of concentrations. At the middle and higher end, however, there was hardly any discrimination betwee different standards, which is required to distinguish between allergic and non-allergic, e.g. for adults (normal range up to 100 U/ml), and teenagers (normal range up to 200 U/ml), respectively. Thus, this curve is clearly suboptimal. The figures also show that reduction of Mab<hIgE>M.323 in the jetting solution down to 0.1 mg/ml did not help. In addition, further reduction of Mab<hIgE>M.323 in the jetting solution down to 0.01 mg/ml provided better dynamics (standard E/D=roughly factor 2, compared to practically no discrimination using higher concentrations, for instance), but signal levels became fairly low, resulting in poor discrimination at the lower end. Moreover, in the absence of a filler substance, reproducibility from one test carrier lot to another was exceedingly poor.

Figure 1:
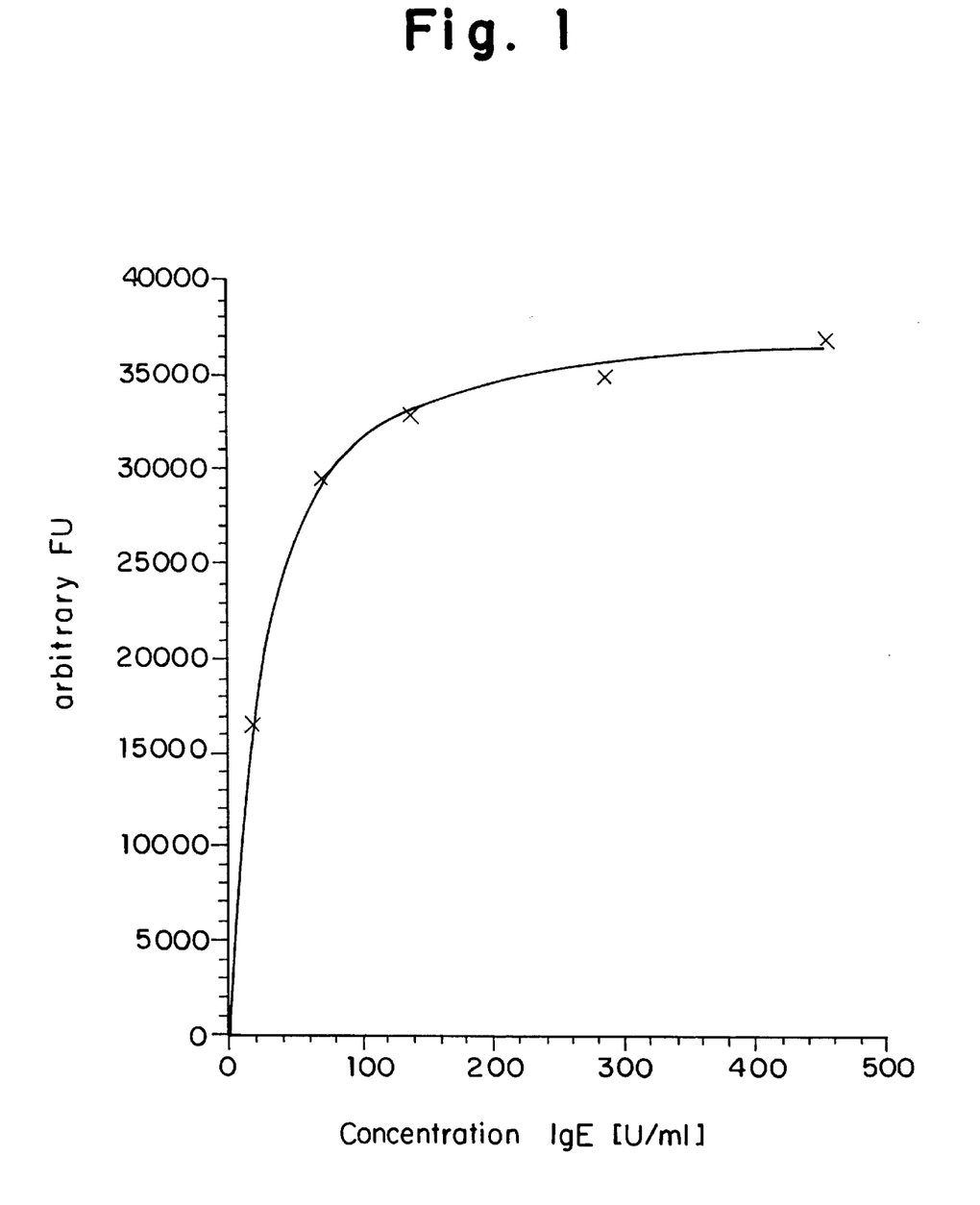
FIGS. 1 to 8 show dose response curves obtained for assays described in the examples.
Figure 2:
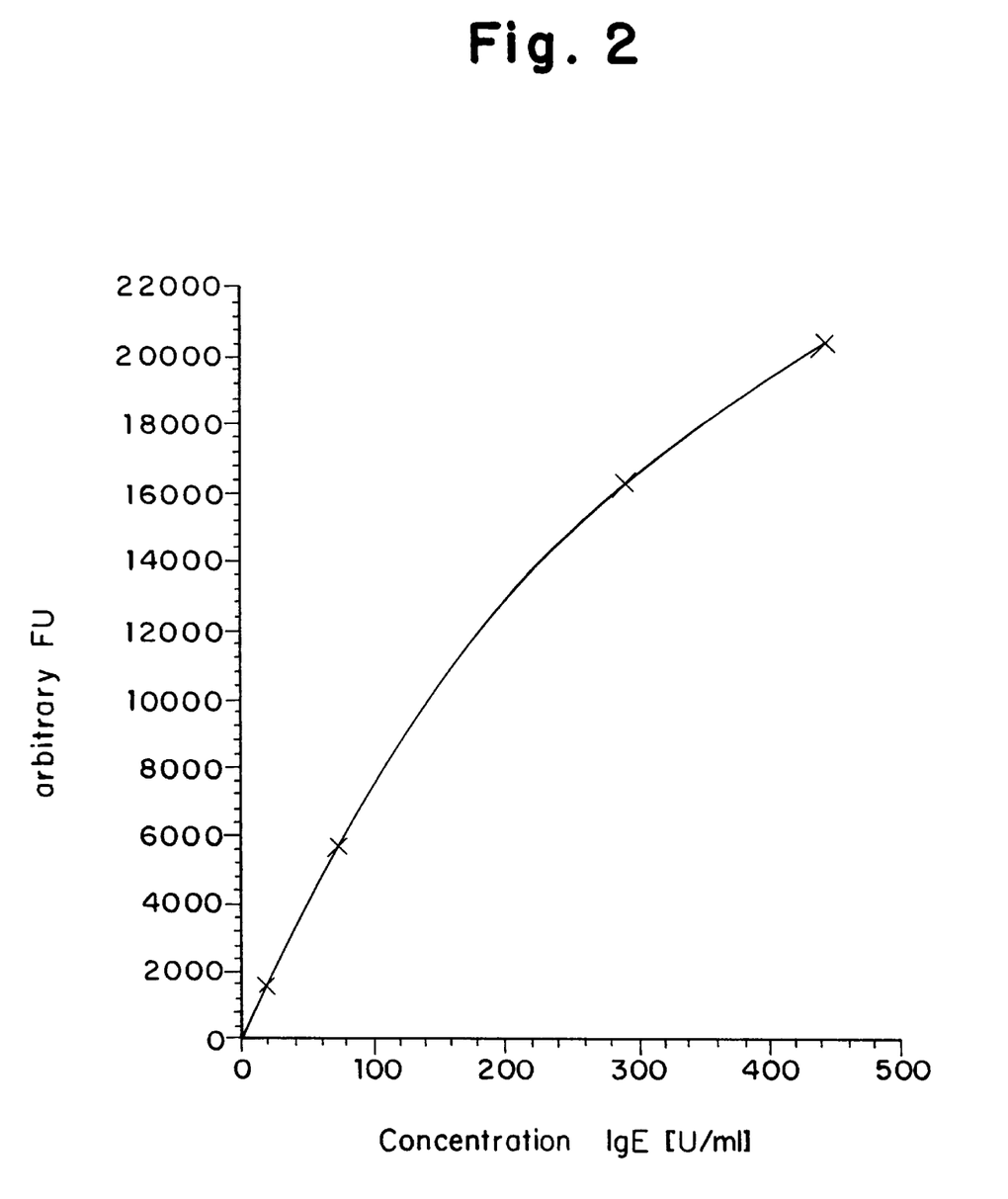

Following these results, concentrations of Mab<hIgE>M.323 in the jetting solution in the range of 0.01–0.1 mg/ml were tested. In this range, 0.05 mg/ml of Mab<hIgE>M.323 in the jetting solution in the presence of 1 mg/ml of filler substance (dummy protein) proved to be optimal, yielding at a satisfactory level of signal a curve with good discrimination across the whole clinically relevant range of concentrations, i.e. good analytical sensitivity in conjunction with broad dynamic range of measurement (see also FIG. 1 & 2).

TABLE 2

|  | ← Mab<hIgE>M.323, [mg/ml] → | | | |
| --- | --- | --- | --- | --- |
| [U/ml] | 0.05 | 0.05 | 0.05 | 0.05 |
| Standard A | 0 | 40 | 99 | 45 | 50 |
| Standard B | 18.6 | 1600 | 993 | 1810 | 1309 |
| Standard C | 72.4 | 5688 | 3834 | 6580 | 4370 |
| Standard D | 145 | — | 7152 | 10797 | 9850 |
| Standard E | 291 | 16317 | 11598 | 17639 | 14022 |
| Standard F | 446 | 20479 | 14439 | 21350 | 15643 |

(different lots of Mab<hIgE>M.7H8-CCOH-latex-conjugate)

Immobilisation of Biotinylated Antibody on Streptavidin Coated Reaction Sites

Test format A:
  5×5 spots of thermo-BSA-Streptavidin conjugate,
  +Mab<hIgE>M.7H8 (IgG)-biotinylated in phosphate buffer.
  => 20 min incubation at RT with orbital shaking.
  => wash (=b/f-separation) myeloma IgE standards in horse serum, 1:2 diluted in phosphate buffer, 50 μl.
  => 20 min incubation at RT with orbital shaking.
  => wash (=b/f-separation).
  +Mab <hIgE>M.09018132-digoxigenylated in phosphate buffer, ≧2 μg/ml, 50 μl.
  => 20 min incubation at RT with orbital shaking.
  => wash (=b/f-separation).
  +conjugate Pab<DIG>S(IgG/IS)—COOH-latex (Y/G), 0.025% solids, 50 μl.
  => 20 min incubation at RT with orbital shaking.
  => wash (=b/f-separation).
  => measurement ($\lambda_{ex}$ 485 nm; $\lambda_{em}$ 530 nm)

Test format B:
  5×5 spots of thermo-BSA-Streptavidin conjugate,
  +Mab<hIgE>M.323 (IgG)-biotinylated in phosphate buffer.
  => 20 min incubation at RT with orbital shaking.
  => wash (=b/f-separation).
  +myeloma IgE standards in horse serum, 1:2 diluted in phosphate buffer, 50 μl.
  => 20 min incubation at RT with orbital shaking.
  => wash (=b/f-separation).
  +Mab <hIgE>M.7H8-digoxigenylated in phosphate buffer, ≧2 μg/ml, 50 μl.
  => 20 min incubation at RT with orbital shaking.
  => wash (=b/f-separation).
  +conjugate Pab<DIG>S(IgG/IS)—COOH-latex (Y/G), 0.025% solids, 50 μl.
  => 20 min incubation at RT with orbital shaking.
  => wash (=b/f-separation).
  => measurement ($\lambda_{ex}$ 485 nm; $\lambda_{em}$ 530 nm)

Variation of the Concentration of Biotinylated Whole IgG

Test format:
  As above, but with different concentrations of biotinylated solid phase antibody in the range of 0.01–7.0 μg/ml As with direct adsorption, problem were initially encountered with spotted streptavidin solid phase and the immobilisation of biotinylated antibody in terms of limited dynamic range of measurement. Indeed, the expansion of measurement range up to some 2000 U/ml, which would be advantageous both in terms of reduction of repeat testing after sample dilution, and better assessment of the severity of allergic reactions, did not appear to be feasible at first. Typical results (given as arbitrary fluorescence units, AU), obtained with both formats (A; B), were as follows:

TABLE 3

| [U/ml] | ← Mab<hIgE>XX-biotinylated [μg/ml] → | | | |
| --- | --- | --- | --- | --- |
|  | 2.0 (A) | 0.5 (A) | 7.0 (B)* | 0.5 (B) |
| Standard A | 0 | 540 | 32 | 678 | 39 |
| Standard B | 18.6 | 4965 | 3464 | 7955 | 2706 |
| Standard C | 72.4 | 12440 | 6778 | 18725 | 5355 |
| Standard D | 145 | 15844 | 8213 | 23815 | 6463 |
| Standard E | 291 | 19090 | 9640 | 25745 | 8265 |
| Standard F | 446 | 20870 | 9999 | 26615 | 8698 |
| Standard G | 2300 | n.d. | 11605 | n.d. | 9555 |

*Mab<hIgE>M.7H8(IgG)-DIG replaced by Mab<hIgE>M.09018132(IgG)-DIG in this case.

Initially, above the level of about 145 U/ml, the curves we obtained were flat, truncating the range of measurement.

However, by adjusting the binding site density by diluting the concentration of biotinylated capture antibody while maintaining a fixed incubation time, we found that the dynamic or linear range of the dose response curve could be substantially expanded, as is shown in the following table for the concentration of 0.03 μg/ml which was found to be optimal:

TABLE 4

Figure 3:
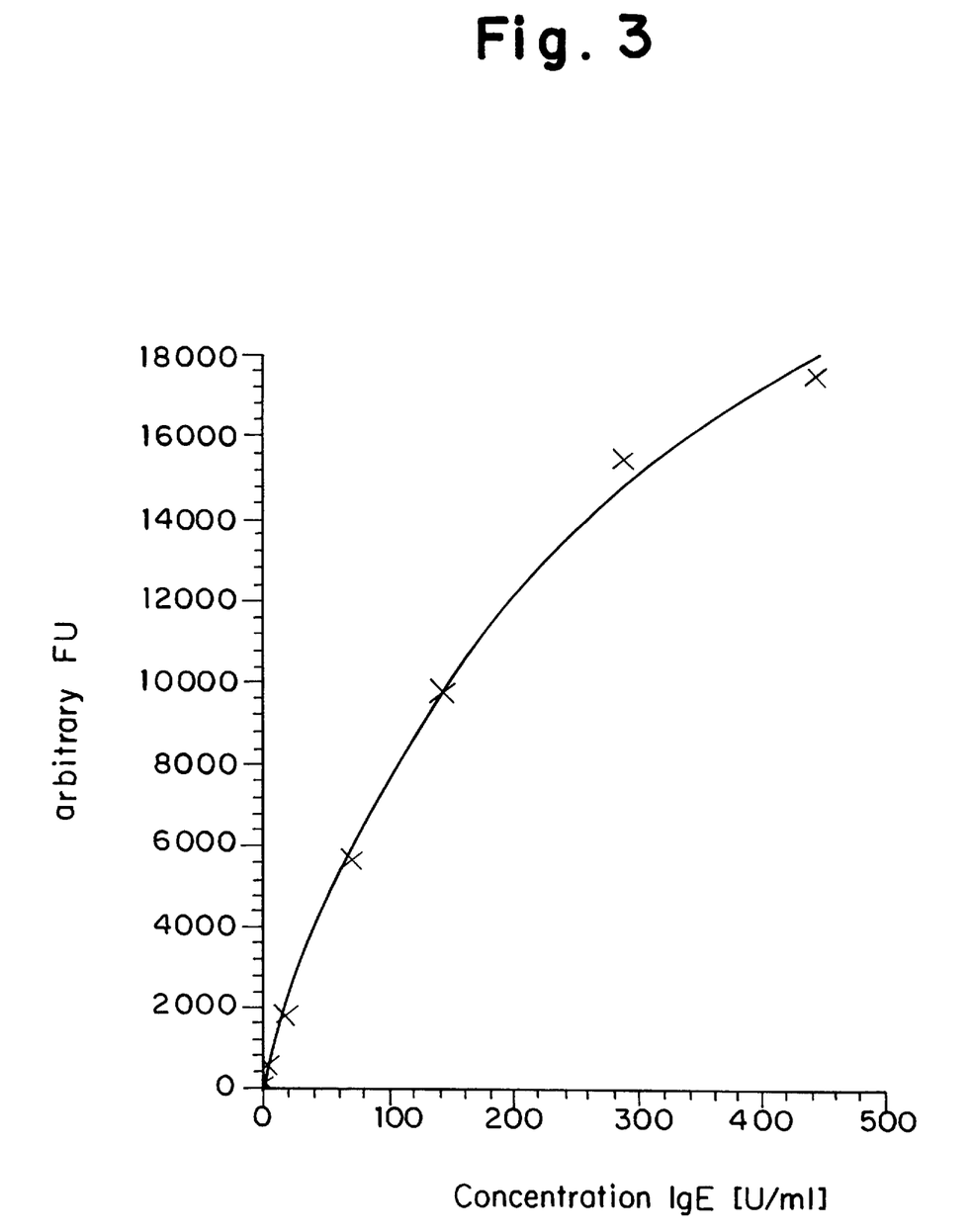
Figure 4:
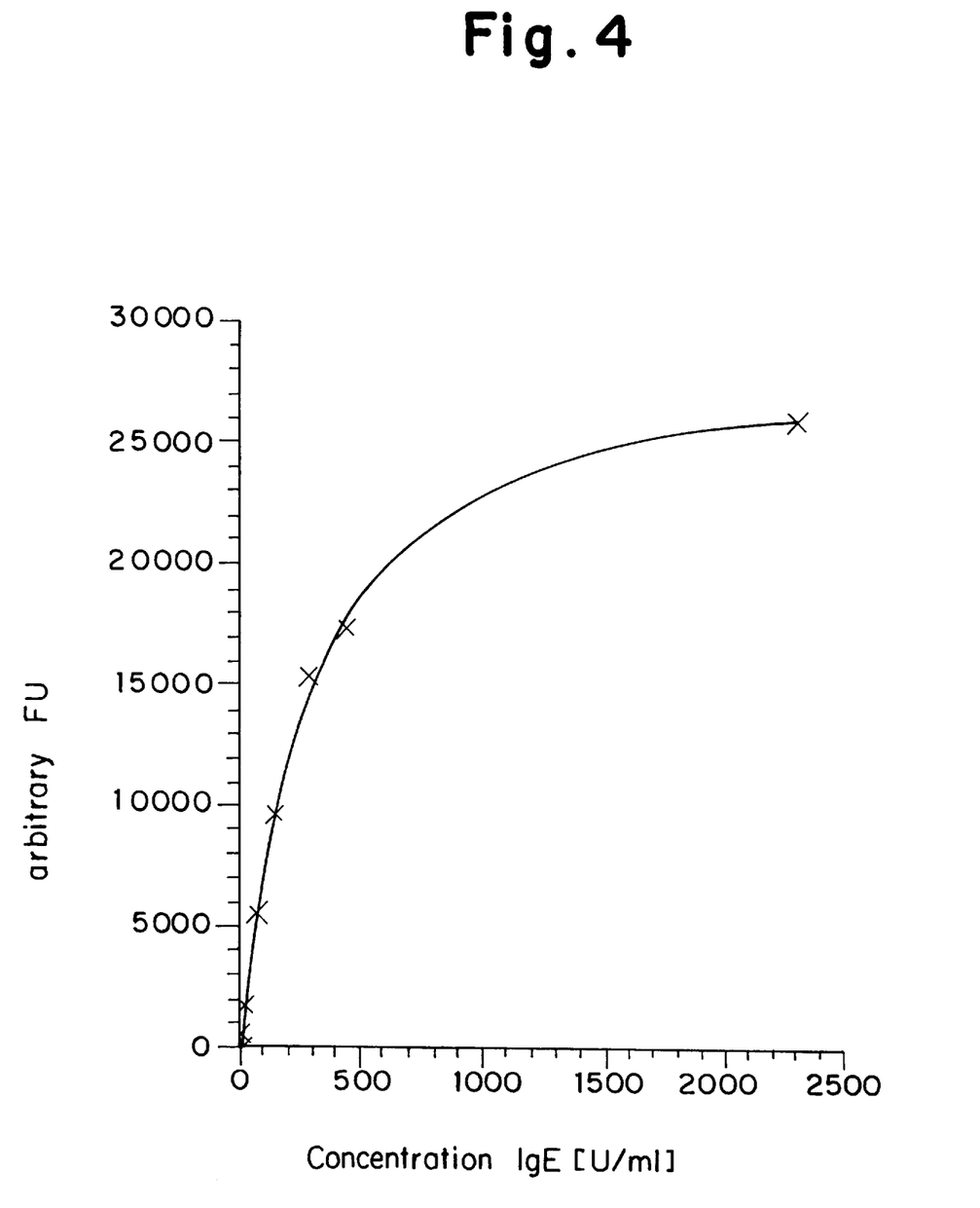

|  | ← Mab<hIgE>XX-biotinylated [μg/ml] → | | | |
| --- | --- | --- | --- | --- |
| [U/ml] | 0.03 (A) | 0.03 (A) | 0.03 (B) | 0.03 (B) |
| Standard A | 0 | 121 | 141 | 38 | 80 |
| Standard B' | 2.9 | 493 | 445 | 311 | 340 |
| Standard B | 18.6 | 1722 | 1698 | 1365 | 1291 |
| Standard C | 72.4 | 5579 | 5498 | 4375 | 4809 |
| Standard D | 145 | 9744 | 9792 | 7649 | 7855 |
| Standard E | 291 | 15479 | 16049 | 11979 | 12594 |
| Standard F | 446 | 17522 | 22710 | 14218 | 15087 |
| Standard G | 2300 | 26269 | 32282 | 23756 | 22175 | see also FIGS. 3 & 4.

Variation of the Incubation Time Using Biotinylated Whole IgG, c=Constant

Test format:
  As above, but with different incubation times (3–39 min/RT) for the reaction of the various reactants, ie biotinylated solid phase antibody, digoxigenylated indicator antibody, and anti-digoxigenin-latex conjugate.

Here, standard G (2300 U/ml) was used as sample to investigate the effect on dose response levels of variable incubation times for different reactants, while maintaining a fixed concentration of reactant, respectively 0.03 μg/ml for biotinylated solid phase antibody, 2.0 μg/ml for digoxigenylated indicator antibody, and 0.025% solids for anti-digoxigenin-latex conjugate.

Figure 5:
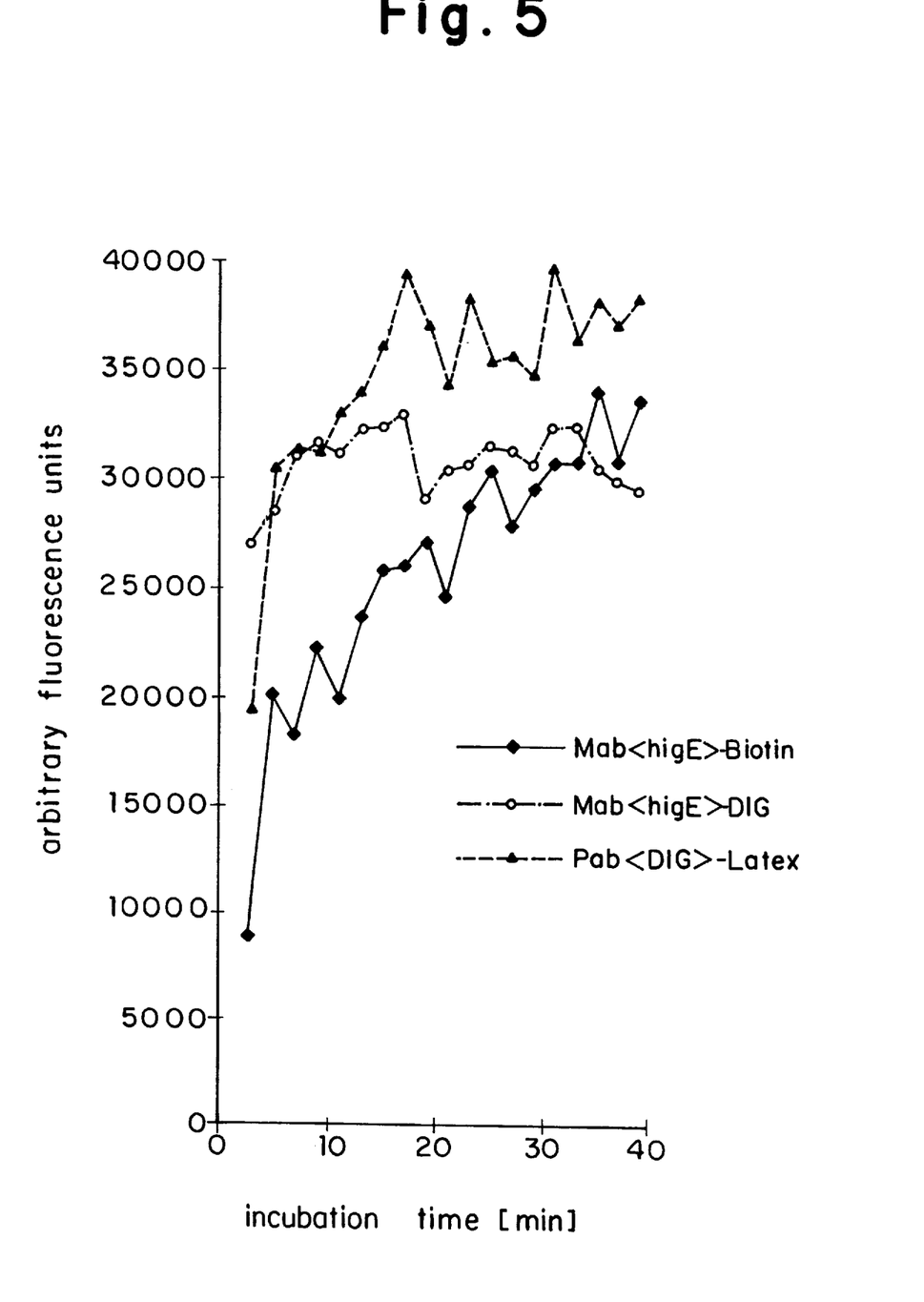

The results of these experiments are illustrated in FIG. 5. These results show that the modulation of the binding site density on the solid phase, i.e. adjustment by means of varying the amount of immobilized reactant (Mab<hIgE>-biotin) that carries those binding sites by varying the incubation time, was the most effective way to modulate the dose response.

Consequently, with only 10 min incubation instead of 20 min at fixed mass per volume of reactant, further dilution of binding site density was used, resulting in marked changes in the linearity, especially in the range 0–450 U/ml, as is illustrated by the incremental increase per standard concentration (standard N/standard N-1); note especially the improvement in the range of standard D/C, E/D, and F/E:

TABLE 5

| | [U/ml] | ← Mab<hIgE>7H8-biotinylated [µg/ml]→ | | |
|---|---|---|---|---|
| | | 0.5 | 0.03/20 min | 0.03/10 min |
| Standard A | 0 | | | |
| Standard B' | 2.9 | 28.70 | 4.07 | 2.20 |
| Standard B | 18.6 | 3.77 | 3.49 | 4.14 |
| Standard C | 72.4 | 1.96 | 3.24 | 3.17 |
| Standard D | 145 | 1.21 | 1.75 | 1.93 |
| Standard E | 291 | 1.17 | 1.59 | 1.84 |
| Standard F | 446 | 1.04 | 1.13 | 1.54 |
| Standard G | 2300 | 1.16 | 1.50 | 1.57 |
| | | 5.57 | 2.40 | 2.34 = AVG |
| | | 10.24 | 1.17 | 0.97 = SD |
| | | 0.04 | 0.34 | 0.57 = LDD |

LDD is expressed in [U/ml] as calculated via linear regression based on mean +2 SD of replicates of zero dose signal.

In this case, due to lower signal levels and reduced steepness (in favour of expanded range of linear and dynamic measurement), analytical sensitivity decreased with increasing dilution of binding site density on the solid phase.

However, it would be possible to adjust the valency of reagents that carry binding sites of interest in order to compensate for the decreased sensitivity, i.e. to achieve the goal of high sensitivity, while retaining good linearity, and broad dynamic range of measurement.

Variation of Valency: Whole IqG-biotin Replaced by Biotinylated Fab-fragment

Test format:

For equal molarity in the reaction mixture, 0.01 µg/ml of Fab (MW≈50000 dalton) instead of 0.03 µg/ml of IgG (MW≅150000 dalton) should be used.

In view of the increased likelihood of sterical hindrance, especially in conjunction with sterically demanding microsphere labels, the concentration of Mab<hIgE>(Fab) was increased in order to approach the goals mentioned above. Yet, with monobiotinylated monovalent Fab, binding sites can be applied to the intended assay at the highest level of purity and characterisation. The following results were obtained with different concentrations:

TABLE 6

| | [U/ml] | ← Mab<hIgE>7H8(Fab)-biotinylated [µg/ml] → | | | |
|---|---|---|---|---|---|
| | | 0.01 | 0.03 | 0.05 | 0.10 |
| Standard A | 0 | 100 | 114 | 87 | 88 |
| Standard B' | 2.9 | 185 | 304 | 434 | 666 |

TABLE 6-continued

| | [U/ml] | ← Mab<hIgE>7H8(Fab)-biotinylated [µg/ml] → | | | |
|---|---|---|---|---|---|
| | | 0.01 | 0.03 | 0.05 | 0.10 |
| Standard B | 18.6 | 480 | 1071 | 2114 | 3346 |
| Standard C | 72.4 | 1631 | 4346 | 7307 | 10781 |
| Standard D | 145 | 4085 | 7945 | 11989 | 18512 |
| Standard E | 291 | 6717 | 12249 | 18769 | 24026 |
| Standard F | 446 | 8441 | 16005 | 23814 | 31904 |
| Standard G' | 1000 | n.d. | n.d. | 31622 | 43192 |
| Standard G | 2300 | 20768 | 34783 | n.d. | n.d. |

The changes in the dose response curve profile are illustrated below using data showing the steepness of the curves as represented by the slope derived from linear regression between two particular points:

TABLE 7

| | | ← Mab<hIgE>7H8(Fab)-biotinylated [µg/ml] → | | | |
|---|---|---|---|---|---|
| | increment | 0.01 | 0.03 | 0.05 | 0.10 |
| slope at | standard B':A | 29.2 | 66.2 | 119.4 | 199.5 |
| slope at | standard B:A | 20.4 | 51.6 | 109.0 | 175.2 |
| slope at | standard F:E | 11.1 | 24.2 | 32.5 | 50.8 |
| slope at | standard G':F | n.d. | n.d. | 14.1 | 20.4 |
| slope at | standard G:F | 6.6 | 10.1 | n.d. | n.d. |
| LDD* [U/ml] | | 0.88 | 0.34 | 0.06 | 0.05 |

* = as calculated via linear regression based on mean + 2 SD of replicates of zero dose signal Thus, at 0.1 µg/ml of Fab, a curve profile was generated that provided for high analytical sensitivity at the lower end as well as good dynamics at the upper end of the standard curve.

In a repeat experiment using 0.1 µg/ml of Mab<hIgE>7H8 (Fab)-biotinylated, this favourable curve profile featuring both high sensitivity (0.05 U/ml) and broad dynamic range of measurement (ca. $5 \times 10^4$ on the level of concentration) could be reproduced:

TABLE 8

| Standard | [U/ml] | bound signal [AU] | incremental increase/slope, lin. regr. (standard N/standard N-1, resp.) | |
|---|---|---|---|---|
| A | 0.0 | 78 | | |
| B' | 2.9 | 689 | 8.83 | 210.69 |
| B | 18.6 | 3519 | 5.11 | 180.25 |
| C | 72.4 | 11315 | 3.22 | 144.91 |
| D | 145.0 | 17256 | 1.53 | 81.83 |
| E | 291.0 | 27144 | 1.57 | 67.73 |
| F | 446.0 | 32905 | 1.21 | 37.17 |
| G' | 1000 | 42413 | 1.29 | 17.16 |
| G | 2300 | 48174 | 1.14 | 5.01 |

Biotinylated Antibody Spotted onto a Thermo-BSA-biotin:poly-streptavidin Coat

This kind of solid phase features tiny spots of test-specific antibody (biotinylated) fixed on top of a special type of streptavidin layer, thus providing simpler test format (3 steps instead of 4 steps as with the previous format using streptavidin spots). Additionally, this assay format provides multi-analyte testing capability due to test-specific individual reaction sites.

Test format:

4×4 spots of <analyte>antibody–biotin/0.5 mg/ml BSA-biotin (=filler protein)+sample (standards, 1:2 diluted in phosphate buffer, 50 µl).

=>20 min incubation at RT with orbital shaking.
=>wash (=b/f-separation)+Mab<analyte>antibody–digoxigenin in phosphate buffer, ≧1 μg/ml, 50 μl.
=>20 min incubation at RT with orbital shaking.
=>wash (=b/f separation) conjugate Mab<DIG>M-19-11 (IgG)-COOH-latex (Jg97), 0.025% solids, 50 μl.
=>20 min incubation at RT with orbital shaking.
=>wash (=b/f separation) measurement ($\lambda_{ex}$ 633 nm, $\lambda_{em}$ 660 nm).

(a) Total-IgE assay

Here, solid phase antibody is either Mab<hIgE>M-_7H8 (Fab)-biotin, or Mab<hIgE>M_323-biotin (IgG and Fab, respectively). Standards are myeloma IgE in horse serum matrix. Upon varying reagent concentration in the spotting solution, the following data (expressed in arbitrary fluorescent units) were obtained:

TABLE 9

| | | ← Mab<hIgE>7H8(Fab)-biotinylated [μg/ml] → | |
|---|---|---|---|
| [U/ml] | 30 | 90 | 300 |
| Standard A | 0 | 28 | 17 | 23 |
| Standard B' | 2.9 | 424 | 595 | 764 |
| Standard B | 18.6 | 1977 | 3186 | 3885 |
| Standard C | 72.4 | 6820 | 8949 | 10985 |
| Standard D | 145 | 11570 | 11982 | 16925 |
| Standard E | 291 | 16848 | 17819 | 22604 |
| Standard F | 446 | 20284 | 21388 | 25280 |
| Standard G | 2300 | 29382 | 27208 | 30589 |

The higher the concentration, the less dynamics at the higher end of the standard curve.

TABLE 10

| | | ← Mab<hIgE>323 Fab)-biotinylated [μg/ml] → | |
|---|---|---|---|
| [U/ml] | 30 | 90 | 300 |
| Standard A | 0 | 24 | 14 | 20 |
| Standard B' | 2.9 | 416 | 893 | 1297 |
| Standard B | 18.6 | 2048 | 4624 | 5973 |
| Standard C | 72.4 | 6335 | 11635 | 15121 |
| Standard D | 145 | 10987 | 16109 | 20976 |
| Standard E | 291 | 16721 | 20150 | 25612 |
| Standard F | 446 | 19012 | 22392 | 27024 |
| Standard G | 2300 | 26348 | 25818 | 29159 |

Thus, in this system, good differentiation is found across the entire standard curve only at 30 μg/ml.

TABLE 11

| | | ← Mab<hIgE>323(IgG)-biotinylated [μg/ml] → | |
|---|---|---|---|
| [U/ml] | 10 | 30 | 100 |
| Standard A | 0 | 143 | 143 | 382 |
| Standard B' | 2.9 | 283 | 520 | 1672 |
| Standard B | 18.6 | 1161 | 2574 | 8905 |
| Standard C | 72.4 | 3899 | 7790 | 18409 |
| Standard D | 145 | 6996 | 11389 | 23230 |
| Standard E | 291 | 10954 | 15051 | 27181 |
| Standard F | 446 | 13680 | 17449 | 28547 |
| Standard G | 2300 | 19298 | 20793 | 29741 |

While practically no dynamics and differentiation in the range of standard E–G was observed with 100 μg/ml of solid phase antibody in the spotting solution, both criteria are met very well using 10 μg/ml.

Thus, the above results confirm that adjusting the solid phase binding site density in this example considerably enhances the working range of the assay at higher concentrations, while still retaining excellent analytical sensitivity at lower concentrations. For instance, using 30 μg/ml of Mab<hIgE>7H8(Fab)-biotin, an LDD of less than 0.01 U/ml results using linear regression at A-B on the basis of 2 SD above mean of replicates of 0-standard, which is more than one order of magnitude below the state of the art.

Figure 6:
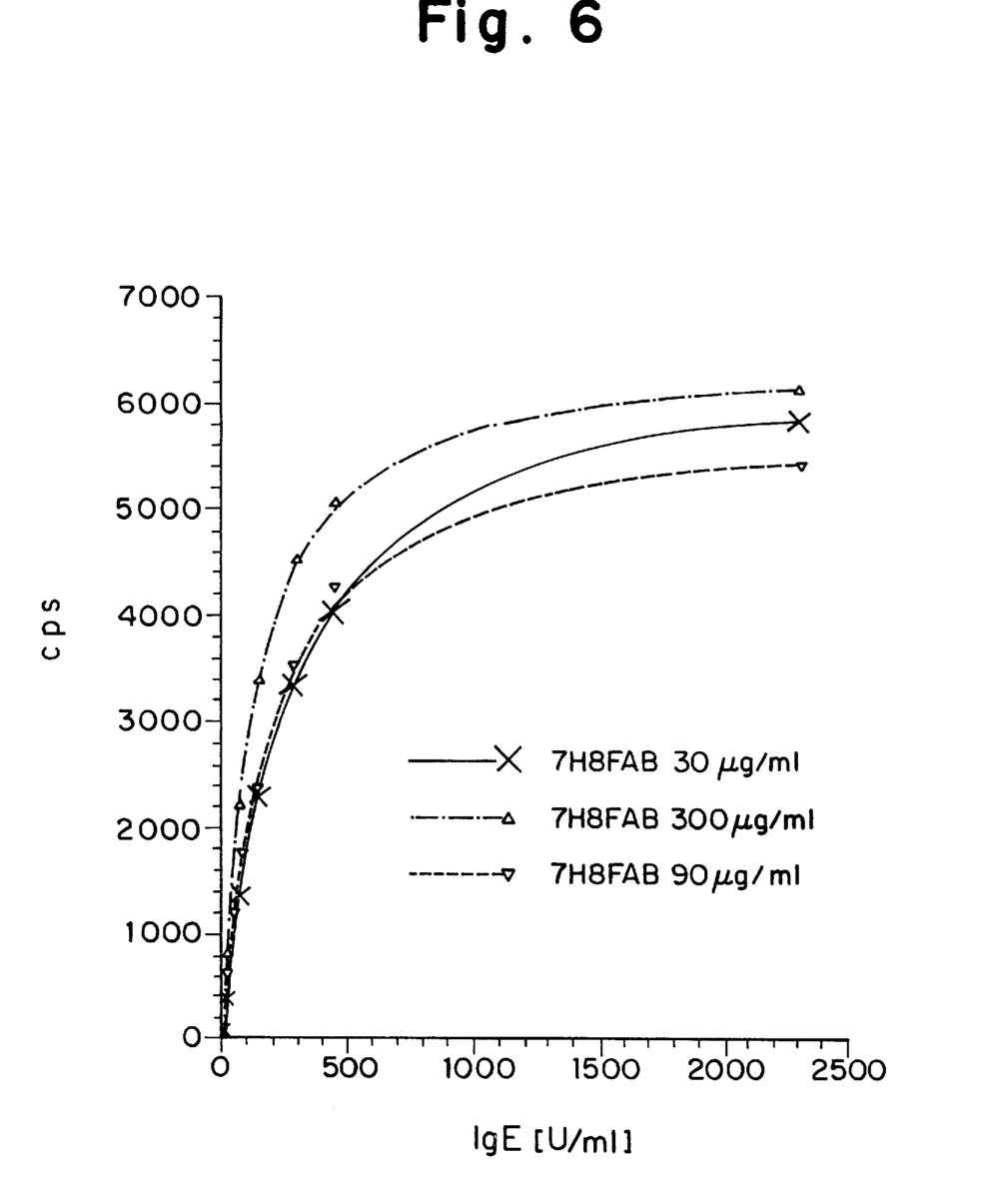
Figure 7:
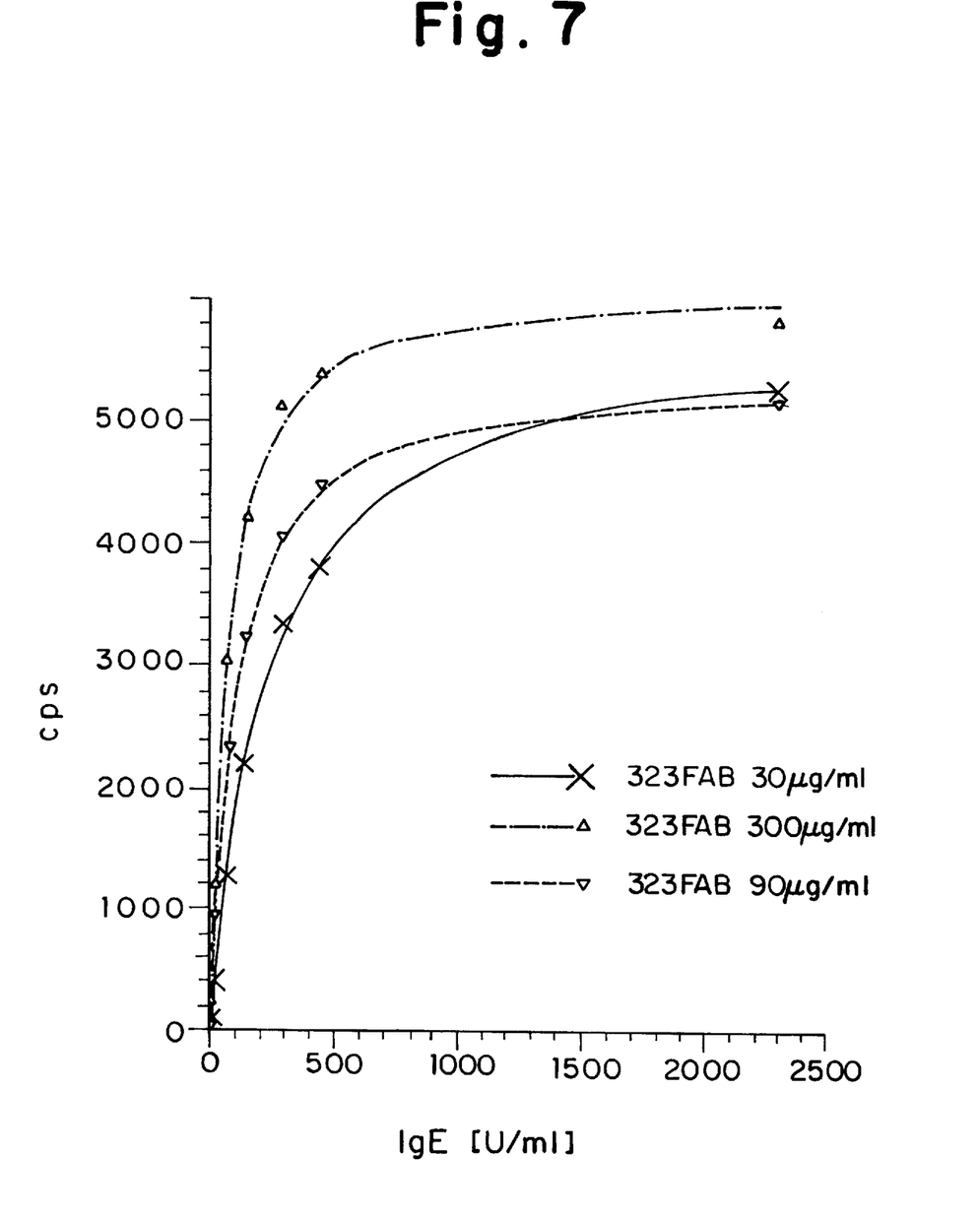
Figure 8:
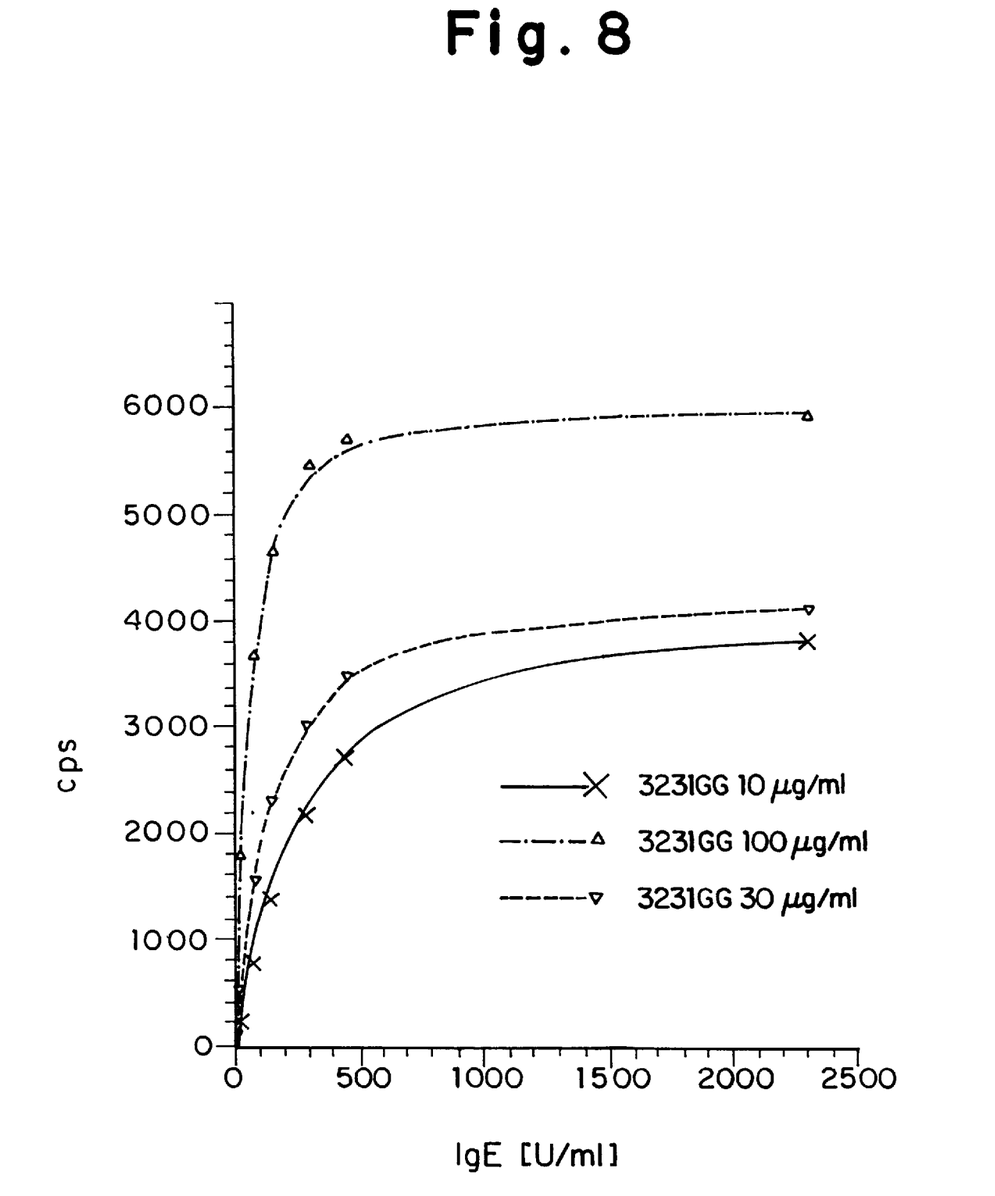

The modulating effects of solid phase binding site density on dose response curve shapes are illustrated in FIG. 6–8.

(b) TSH assay

Here, Mab<TSH>M_1.20(Fab')$_2$-biotin is employed as solid phase antibody. Standards are different doses of hTSH in BSA matrix. Upon varying reagent concentration in the spotting solution, the following data (expressed in arbitrary fluorescence units) were obtained:

TABLE 12

| | ← Mab<TSH>1.20(Fab')$_2$-biotinylated {μg/ml] → | | | |
|---|---|---|---|---|
| [μU/ml] | 0.5 mg/ml | => S/N | 0.1 mg/ml + 0.5 mg/mlBSA biotin > S/N | |
| Standard A | 0.0 | 181 | | 69 | |
| Standard B | 0.22 | 435 | 2.4 | 263 | 3.8 |
| Standard C | 2.80 | 2232 | 12.3 | 1539 | 22.2 |
| Standard D | 6.90 | 4848 | 26.7 | 3440 | 49.7 |
| Standard E | 19.42 | 9201 | 50.8 | 7516 | 108.6 |
| Standard F | 40.41 | 14336 | 79.2 | 11509 | 166.9 |

Thus, this example shows that diluting test-specific solid phase binding sites, significantly improves the steepness of the standard and greatly reduces non-specific binding, while sacrificing only a little specifically bound signal.

While the examples are provided to demonstrate the present invention, the methods described above are applicable, alone or in combination, to the optimisation of other binding assays.

The references mentioned herein are hereby incorporated by reference in their entirety.

I claim:

1. A process for manufacturing an assay kit for performing a microspot binding assay, said assay using a binding agent having binding sites specific for an analyte, said binding agent being immobilized on a solid phase in the form of a plurality of microspots, said process comprises the steps of:

(a) determining a first dose response curve for a given density of binding agent on said solid phase in the form of a microspot;

(b) altering the density of said binding agent on said solid phase in the form of a microspot to provide a diluted density of binding sites in said microspot and thereby modulate the dose response curve;

(c) determining a dose response curve for said reduced density;

(d) optionally repeated steps (b) and (c);

(e) selecting a diluted density of binding agent on said solid phase in the form of a microspot which provides an extended working range, and improved precision, with respect to the first dose response curve; and (f) immobilizing binding agent having binding sites specific for an analyte on a solid phase in the form of a plurality of microspots, to provide two or more different densities of binding sites for said analyte, each of said two or more different densities being selected in accordance with steps (a) to (e).

2. The process of claim 1, wherein said binding agent is immobilized by direct adsorption on said solid phase.

3. The process of claim 1, wherein said solid phase is activated and said binding agent is functionalized such that said solid phase is capable of capturing said binding agent, said binding agent being immobilized on said solid phase prior to said assay.

4. The process of claim 1, wherein said solid phase is activated and said binding agent is functionalized such that said solid phase is capable of capturing said binding agent, said binding agent being immobilized on said solid phase during said assay.

5. The process of claim 4, wherein said solid phase is activated by coating all or a part of it with capture agent selected from the group consisting of streptavidin or avidin and said binding agent is functionalized by attachment to biotin.

6. The process of claim 4, wherein said solid phase is activated by coating all or a part of it with biotin and said binding agent is functionalized by attachment to a functionalizing agent selected from the group consisting of streptavidin or avidin.

7. The process of claim 4, wherein said binding agent is applied to said solid phase in a liquid carrier and the density of said binding sites is altered by altering the concentration of said binding agent in said liquid carrier.

8. The process of claim 7, wherein said binding agent is immobilized by spraying droplets containing said binding agent on said solid phase and the density of said binding sites on said solid phase is adjusted by varying the concentration of binding agent or volume of said droplets containing said binding agent.

9. The process of claim 8, wherein said droplets are applied to said solid phase using an ink jet printer.

10. The process of claim 7, wherein said liquid carrier includes a inert filler substance.

11. The process of claim 1, wherein the density of said binding sites on said solid phase is adjusted by changing the incubation time during which said binding agent is exposed to said solid phase.

12. The process of claim 1, wherein the density of binding sites on said solid phase is adjusted by changing the valency of said binding agent.

13. The process of claim 1, wherein binding agents having binding sites specific for different analytes are immobilized on said solid phase in the form of a plurality of microspots.

14. A process for determining the concentration of the analyte in a liquid sample comprising the steps of:
   (a) contacting the solid phase of an assay kit manufactured in accordance with claim 1 with a liquid sample so that a fraction of the binding sites are occupied by analyte in the sample;
   (b) measuring a value of a signal representative of the fraction of the binding sites occupied by the analyte; and
   (c) comparing the value of a dose response curve to determine the concentration of the analyte in the liquid sample.

15. A device for use in a binding assay manufactured in accordance with the process of claim 1, said device comprising:
   (a) a solid phase;
   (b) binding agent immobilized on said solid phase said binding agent providing binding sites specific for an analyte, wherein the binding sites are immobilized at two or more microspots, and the density of the binding sites on the solid phase is different at the two or more microspots.

16. A device as claimed in claim 15, said device comprising:
   (a) a solid phase;
   (b) two or more different binding agents immobilized on said solid phase in the form of different microspots, each different binding agent providing binding sites specific for a different analyte, wherein each different binding agent is immobilized at two or more microspots, and the density of the binding sites on the solid support is different at the two or more microspots.

* * * * *